United States Patent [19]
Gayet et al.

[11] Patent Number: 5,593,408
[45] Date of Patent: Jan. 14, 1997

[54] VERTEBRAL INSTRUMENTATION ROD

[75] Inventors: Louis E. Gayet, Saint-Benoît; Yves Rideau, Gisse, both of France

[73] Assignee: Sofamor S.N.C, Rang Du Fliers, France

[21] Appl. No.: 346,902

[22] Filed: Nov. 30, 1994

[51] Int. Cl.$^6$ .................................................. A61B 17/56
[52] U.S. Cl. ............................................. 606/61; 606/73
[58] Field of Search ............................ 606/61, 69, 60, 606/72, 73

[56]  References Cited

U.S. PATENT DOCUMENTS

| | | | |
|---|---|---|---|
| 4,887,595 | 12/1989 | Heinig et al. | 606/61 |
| 5,217,461 | 6/1993 | Asher et al. | 606/61 |
| 5,360,429 | 11/1994 | Jeanson et al. | 606/61 |

*Primary Examiner*—Guy V. Tucker
*Attorney, Agent, or Firm*—Woodard, Emhardt, Naughton, Moriarty & McNett

[57]  ABSTRACT

This rod is made up of a first cylindrical part, being a lumbosacral part (6), which is rigid in all directions, a second part, being a dorsal part (7), which is rigid in a frontal plane, in order to prevent scoliosis, and flexible in a sagittal plane, and a dorsolumbar transition zone (8) connecting the lumbar and dorsal parts and profiled in a progressive manner so that its thickness in the sagittal plane diminishes progressively and its width in the frontal plane increases progressively: this profile is such that the second moment of area of the transition zone reins substantially constant over its entire length. The profile, thus defined, of the transition zone has the aim of avoiding, to a great extent, the risks of breaking due to the fatigue in this zone, resulting from the various movements of the patient in a chair, in particular the flexion/extension movements in a sagittal plane, promoted by the rectangular profile of the dorsal part of the rod.

29 Claims, 4 Drawing Sheets

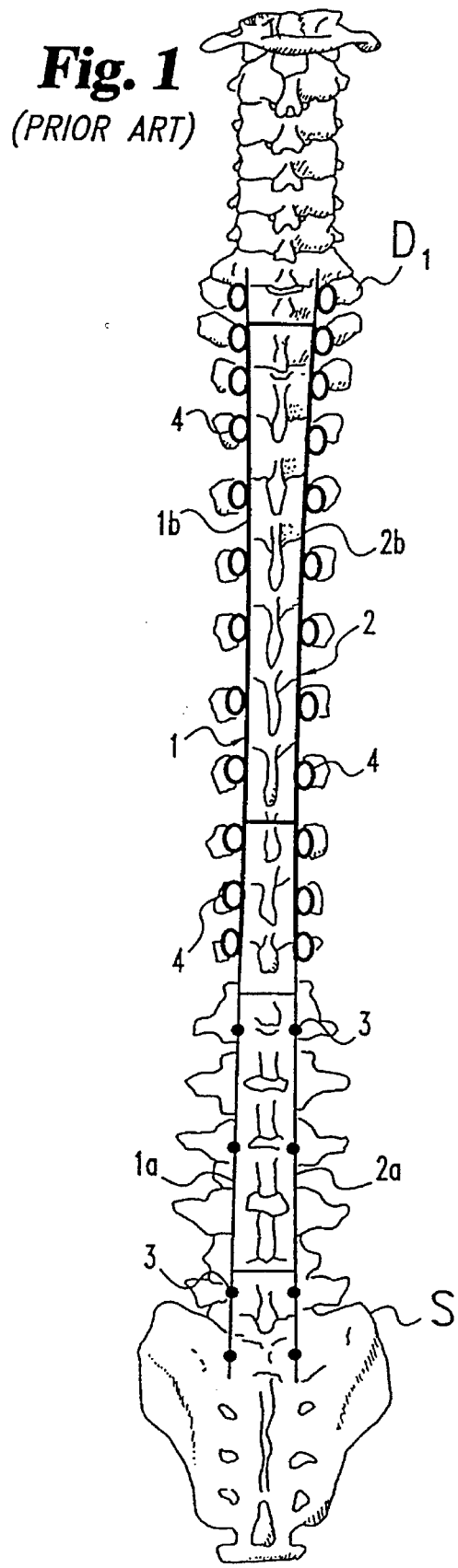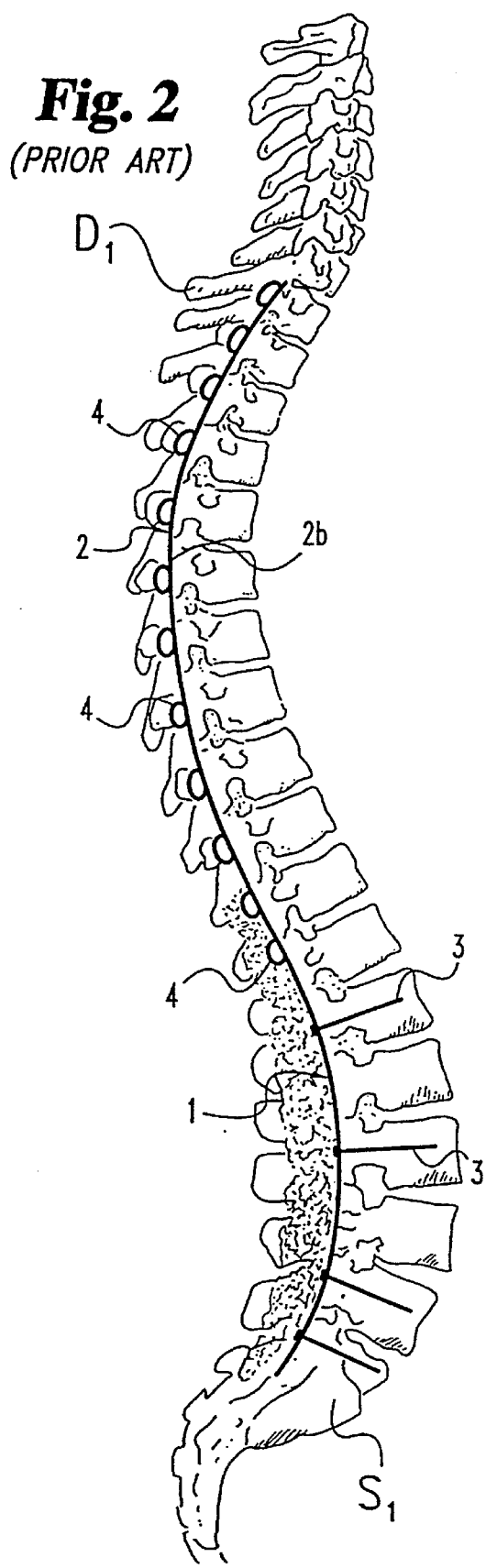

VERTEBRAL INSTRUMENTATION ROD

FIELD OF THE INVENTION

The present invention relates to a vertebral instrumentation rod for the early fixation of an unstable spine, in its growth phase, in patients suffering from muscular dystrophy or myopathy.

BACKGROUND OF THE INVENTION

It is known that children suffering from muscular dystrophy are most often affected by a very severe form, Duchenne's muscular dystrophy (DMD). Due to the fact that the muscles of the trunk are attacked, these children almost all develop scoliosis.

The main characteristic of DMD lies, moreover, in the constant presence of a progressive respiratory insufficiency, the principal factor in a poor life prognosis. The current therapeutic advances in this field permit survival for a great many years. This explains the extreme importance of providing improved comfort in the seated position; the preservation of the serious deformations of the spine, sagittal (kyphosis) or frontal (scoliosis), is thus imperative.

As a result of this progressive respiratory insufficiency, as well as cardiac problems at a relatively advanced stage of DMD, the anaesthetic risks become much greater starting from an average age of about 13–14 years, a period in which the worsening of the scoliosis becomes very marked. It is for this reason that it has been proposed, since 1982, to treat this spinal deformation when the first signs appear indicating with certainty the future presence of scoliosis. Thus, all children with DMD can, without exception, benefit from surgical treatment of the spine: the more severe the DMD, the earlier the intervention will be.

The aim is therefore to fix a spine in its growth phase, seeking a preventive effect rather than a corrective effect, with the need to take into consideration a physiological position of the pelvis, the condition for maintaining a satisfactory equilibrium of the trunk in a permanent manner. The period of operability is situated, on average, between 10 and 13 years of age.

Moreover, this instrumentation must therefore be designed in such a way as to fulfil a double function: maintain spinal stability in the frontal plane and ensure a certain anteroposterior mobility, or mobility in the sagittal plane. This degree of spinal mobility promotes a balancing of the trunk, which improves the functional possibilities of the upper limb. Indeed, obtaining too rigid a spine constitutes an additional functional handicap, when the function of the upper limbs is greatly impaired.

The instrumentation developed by LUQUE is thus known, which extends over the lumbar and dorsal spine and consists of two L-shaped rods, connected at each level to the posterior arches of the vertebrae by metal wires placed around the laminae. The stresses are at their maximum on the steel wires at the ends of the rod effecting the convexity, and on the steel wires at the middle of the rod effecting the concavity. This instrumentation makes it possible in theory to restore a good curvature in the sagittal plane (lumbar lordosis and dorsal kyphosis), but the experience gained reveals a great many long-term problems with this instrumentation.

Complications have been noted for example, such as migration or breaking of the rod in a relatively large number of cases, after periods of six months to three years.

The instrumentation developed by COTREL-DUBOUSSET is also known, the lumbar part of which is firmly fixed, while the thoracic or dorsal part follows the segmental vertebral fixation of Luque, without arthrodesis, in order to permit the growth of this part of the spine. A relatively large number of material defects have been observed with this instrumentation, in particular fatigue breaks in rods stressed by considerable mobility of the truck of the patient. Moreover, with these known types of instrumentation, the growth of the spine provokes a crankshaft effect in the thoracic part, which means that it is not possible to control all the pathological curvatures at this level.

The principal causes of breaking found in conventional rods are the following: fatigue failure if there is no posterior arthrodesis and if the equipment is too rigid or if the stresses are not well distributed; diameter and resistance of the rod too low; insufficient restoration, or no restoration, of lumbar lordoses and dorsal kyphoses in the sagittal plane.

This latter point is very important, since poor restoration of the lumbar lordosis compromises the entire equilibrium of the superjacent spine. A substantial residual kyphotic curvature in fact subjects the rods to considerable stresses and clearly promotes the subsequent breaking. The breaks suffered by the rod are more frequent at the level of the dorsolumbar hinge. In the flexion/extension movement, the lumbar spine has a greater amplitude than does the dorsal spine, which is controlled more by the costal grill.

SUMMARY OF THE INVENTION

The principle of the invention presented here is therefore to use two rods which are designed in such a way as to prevent foreseeable scoliosis from developing and to permit a certain mobility of the subject in the sagittal plane. The intervention is by definition carried out at an early stage, before the surge in spinal growth, in order to avoid as far as possible the operating risks which are always present at a more advanced stage of DMD. The mechanical objective is to propose rods which afford resistance over the course of time, in particular at the level of the dorsolumbar hinge which is under threat.

According to the invention, the vertebral rod comprises a first part, being a lumbosacral part, which is rigid in all directions, a second part, being a dorsal part, which is rigid in a frontal plane, in order to prevent scoliosis, and more flexible in a sagittal plane. These two parts, of different profiles, are connected via a dorsolumbar transition zone which is profiled in a progressive manner so that its second moment of area remains as constant as possible in the said zone.

Thus, between the two different shapes of the rod, an optimized mode of transition is afforded which offers resistance in order to avoid the risks of fatigue failure.

According to one embodiment of the invention, the lumbosacral part is cylindrical and has a toughened surface, the dorsal part is of rectangular cross-section, the greater length of which extends in the frontal plane, the transition zone having a cross-section which becomes progressively rectangular and diminishes starting from the end of the cylindrical part, and the profile of which is such that its second moment of area remains substantially constant over the entire length of this transition zone.

According to a complementary characteristic of the invention, the thickness of the dorsal part, that is to say its width in the sagittal plane, diminishes progressively from the transition zone up to its free end, whereas its length in the frontal plane increases progressively, in order to ensure easy positioning, then decreases progressively up to its free end, near the cervical vertebrae.

BRIEF DESCRIPTION OF THE DRAWINGS

Other particular features and advantages of the invention will emerge from the description which follows and in which reference is made to the attached drawings which illustrate one embodiment thereof by way of non-limiting example.

FIG. 1 is a rear elevation view of a spine fitted with instrumentation defined as a function of known surgical treatment of the spine in DMD, for early fixation in its growth phase.

FIG. 2 is a side elevation view of the spine and of the instrumentation in FIG. 1.

DETAILED DESCRIPTION OF THE INVENTION

Figure 3:
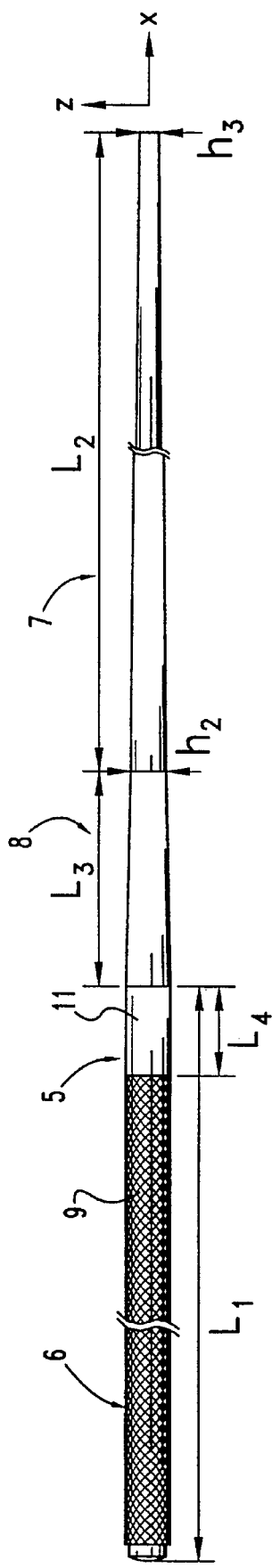
FIG. 3 is a broken longitudinal elevation view of an embodiment of the vertebral rod according to the invention, assumed to extend in a frontal plane.
Figure 4:
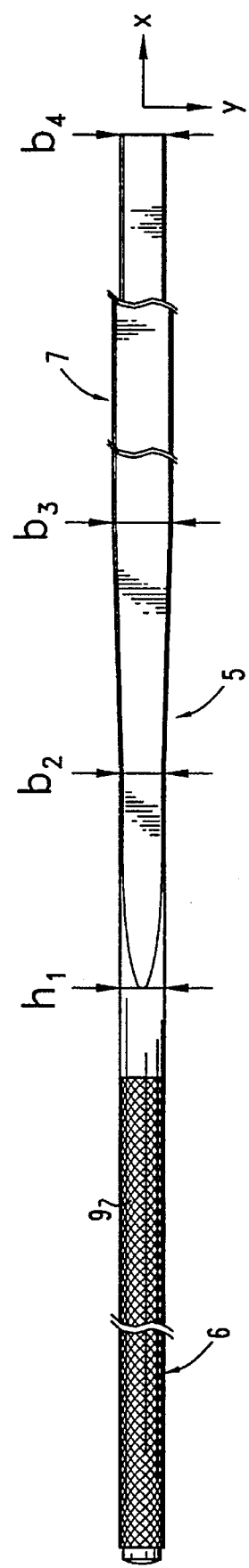
FIG. 4 is a plan view of the rod in FIG. 3.
Figure 10:
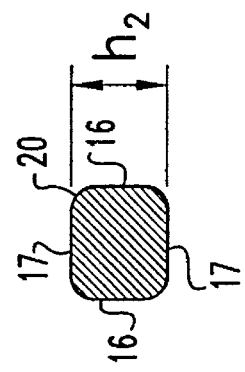
FIGS. 6 to 10 are cross-sections of the transition zone along the cutting lines 6.6, 7.7, 8.8, 9.9, 10.10 in FIG. 5.
Figure 9:
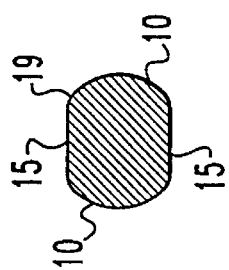
Figure 5:
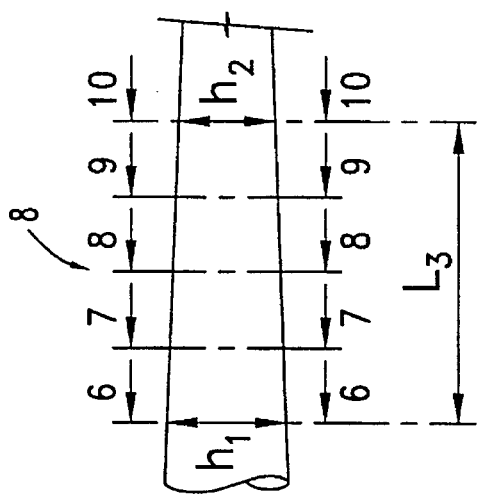
FIG. 5 is a partial elevation view, on an enlarged scale, of the transition zone of the rod in FIGS. 3 and 4.
Figure 8:
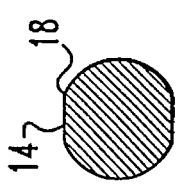
Figure 7:
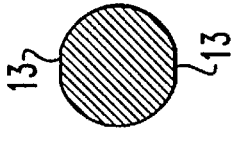
Figure 6:
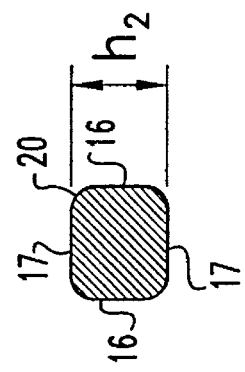

Before proceeding to the description of the vertebral rod illustrated in the drawings, it will be appropriate to set out in greater detail the specifications which it must satisfy:

1. Two requirements, namely mechanical and functional, must be distinguished:

1.1 Lower region (lumbar and sacral): maximum rigidity and strength (correction of initial scoliosis and lumbar kyphosis). Posterior arthrodesis performed in the majority of cases.

1.2 Upper region (dorsal): maximum flexibility and strength (control of the reverse curvature or of a second dorsal curvature inverse to the lumbar curvature). There is no arthrodesis here, and instead a flexibility increasing from distal to proximal is sought.

2. Surgical treatment is possible only during a limited period of time, and in a great many cases follow-up surgery is impossible. The equipment must therefore be reliable and withstand fatigue in children operated on at an age markedly below the average for spinal treatment.

3. The rods with a partially smooth surface must not break, which entails determining their diameter with precision and taking into consideration the possibility of work-hardening and a reduction in the depth of the asperities. If, despite everything, a subsequent break occurs, the assembly must make it possible to control any migration of the equipment, which means taking ito consideration an increase in the number of the transverse traction devices (DTT). From a mechanical point of view, the rods must be rigid in the frontal plane (limitation of the lateral inclination) and horizontal plane (limitation of torsion), more flexible and resistant in the sagittal plane (from C7 to D9), in the upper part of the assembly where the stresses must be distributed uniformly; as regards the threatened zone (dorsolumbar hinge), from D9 to L1, the resistance must be increased.

FIGS. 1 and 2 illustrate known instrumentation of the COTREL-DUBOUSSET type, consisting of two rigid rods 1 and 2 which extend from the sacrum S to the upper dorsal vertebra D1. These rods are rigid, and each consists of a lumbar part 1a, 2a secured by means of pedicular screws 3 to achieve arthrodesis, and of a dorsal part 1b, 2b which has a diameter greater than that of the lumbar part 1a, 2a.

The dorsal parts 1b, 2b pass freely through rings 4 fixed to the vertebrae in a manner known per se in such a way that they do not impede the growth of the dorsal spine.

An embodiment of the rod according to the invention will now be described with reference to FIGS. 3 to 10.

The rod 5 comprises a first part, being a lumbosacral part 6, which is rigid in all directions and extends over a length L1, a second part, being a dorsal part 7, extending on a length L2, which is rigid in a frontal plane (ox,oz) (FIG. 11) and flexible in a sagittal plane (ox, oy), and, finally, a dorsolumbar transition zone 8, extending over a length L3 and connecting the two parts 6, 7. This transition zone 8 is profiled in a progressive manner so that its moment of inertia, that is to say its second moment of area, remains as constant as possible in the said zone.

In the embodiment illustrated in the drawings, the lumbosacral part 6 is cylindrical and has, over the greater part of its length, a roughened surface 9, namely a hurling in the example shown. This roughened surface 9 extends from the sacral end of the part 6 and stops before the start of the transition zone 8 in such a way as to leave, between the latter and the end of the roughened surface 9, a smooth part 11 of length L4.

The transition zone 8 has a cross-section which becomes progressively rectangular and decreases from the end of the cylindrical part 11, as illustrated in FIGS. 5 to 10. Thus, at the limit between the zones 11 and 8, the cross-section 12 is circular, after which flattened surfaces 13 appear on the diametrally opposite sides, the width of these flattened surfaces 13 increasing (flattened surfaces 14, 15 in FIGS. 8 and 9). At the end of the transition zone 8, the cylindrical sides 10 situated between the flattened surfaces 15 are transformed in turn into flattened surfaces 16 in order to form, with the complementary flattened surfaces 17, a rectangular cross-section. It should be noted that as soon as the flattened surfaces 13 appear, the ridges connecting these to the cylindrical sides are progressively rounded (18, 19, 20).

At the same time, from the start to the end of the transition zone 8, the thickness or height h of the rod, which extends in a sagittal plane once positioned on the spine, diminishes progressively from an initial height h1 to a reduced final height h2. The profile, thus formed, of the transition zone 8 is such that its moment of inertia, hence its second moment of area, remains substantially constant over the entire length L3.

Finally, the height h3 of the dorsal part 7 diminishes progressively from the transition zone 8 to its free end, where it has a height h3. The width b in the frontal plane of this dorsal part 7 correspondingly increases progressively from a width b2 (FIG. 4) up to a maximum width b3, then decreases progressively to a width b4 at its free end.

It will be understood that the progressive diminution in the height h in the sagittal plane (ox, oy) confers upon the dorsal part 7 a certain flexibility in this sagittal plane, allowing the patient flexion/extension movements. In contrast, the increase in the width b of the dorsal part 7 in the frontal plane (ox, oz) confers upon it a rigidity in this plane, which makes it possible to prevent the development of scoliosis.

A more detailed description will now be given of an embodiment of a rod 5, and in particular of its transition zone 8 which must be formed in such a way as to eliminate, almost completely, any risk of breaking at this level. This rod can be made of a suitable bio-compatible metal or biocompatible metal alloy, for example of work-hardened austenitic stainless steel 316L, which has the following characteristics:

YOUNG's modulus: E=200,000 MPa
POISSON's ratio: V=0.21
limit of elasticity: $R_{o,x}$=900 MPa
breaking stress: Rm=1050 MPa
endurance limit: Rv=350 MPa
at 5,000,000 cycles.

Figure 12:
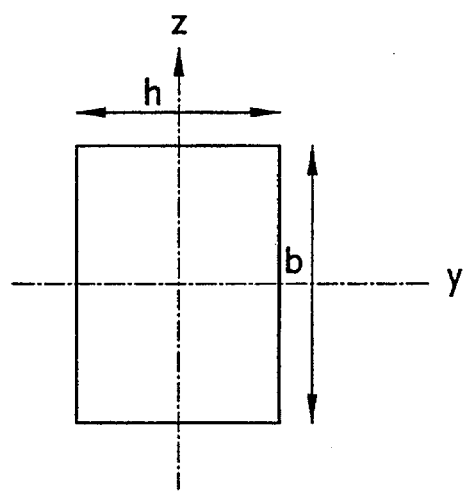
FIG. 12 is a section along 12.12 in FIG. 11.
Figure 11:
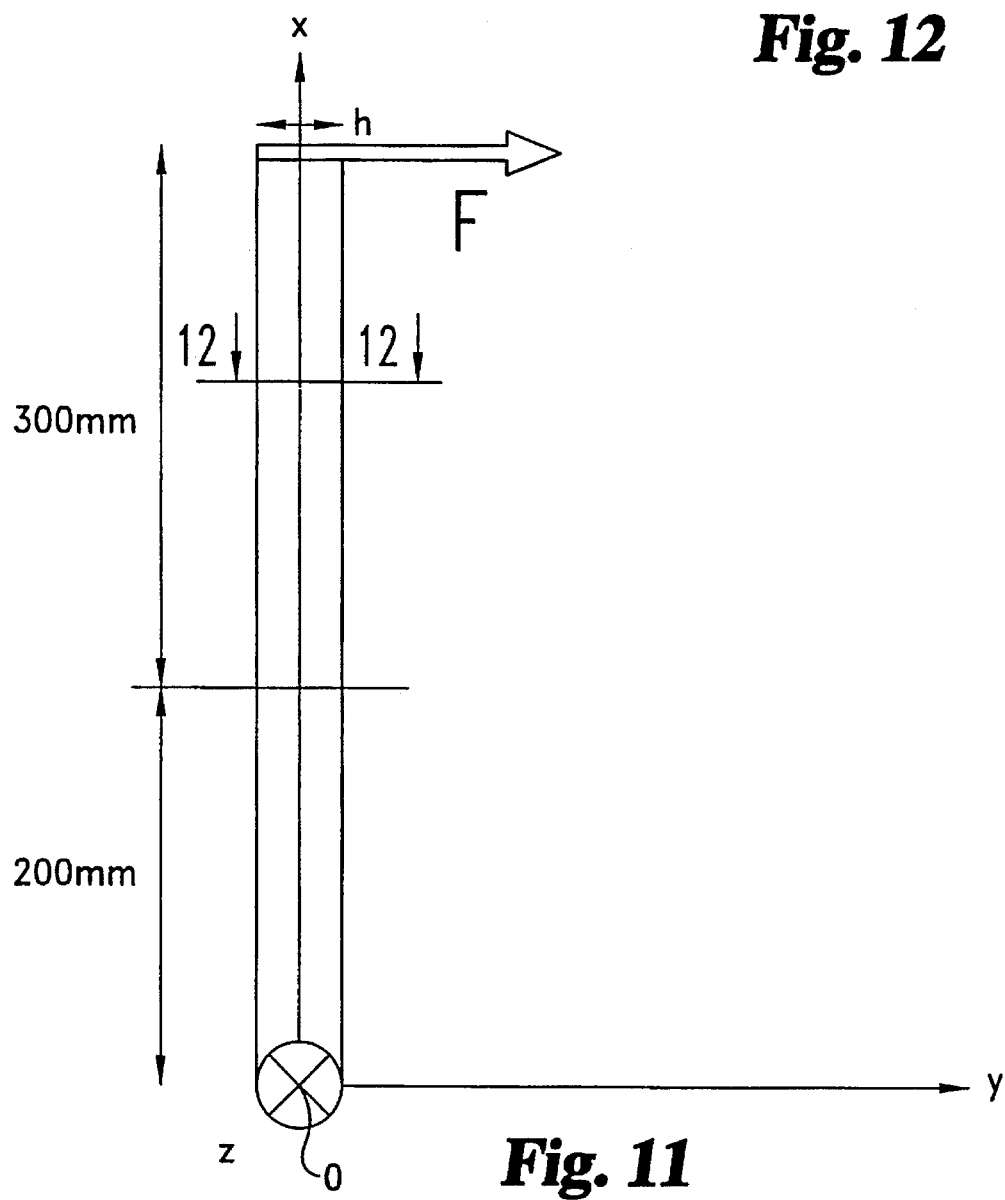
FIG. 11 is a diagrammatic elevation view, in a frontal plane, of a vertebral rod consisting of a cylindrical part and of a rectangular part, the latter here being represented with a constant width in the frontal plane, for reasons of simplification, and the three axes defining the frontal, sagittal and horizontal planes being represented.

FIGS. 11 and 12 illustrate the reference (Ox,y,z) associated with a rod of length L=500 mm, represented in a simplified manner as consisting of a cylindrical part which has a length of 200 mm, and of a rectangular part which has a length of 300 mm.

Study of the rigidity R of the rod:

If a force F is exerted at the end of the rod, the rigidity R of the rod is equal to:

R=F/f, f being the maximum deflection of the rod.

Moreover, f=α/EI where E is the YOUNG modulus of the rod in question, I its second moment of area, and α the angle between the initial and deflected positions of the rod.

The rigidity thus depends on I (second moment of area of the section, on which it is possible to act in order to fulfil the specifications).

The rigidity in the cylindrical section, which corresponds to a proximal part of the rod, having a diameter of, for example, d=5 mm, will thus be directly proportional to the second moment of area I $$I=\pi d4/64=30.68 \ mm^4$$

The rigidity in the rectangular section, which corresponds to the distal part of the rod, will also be directly proportional to the second moment of area; during flexion/extension movements in the sagittal plane, the second moment of area I is equal to:

$$I\ z=b\ h^3/12$$

During flexion/extension movements in the frontal plane, that is to say in fact during the movements of lateral inclination of the rod, the second moment of area will be equal to:

$$I\ y=h\ b^3/12$$

Study of the resistance of the rod:

The maximum stress is L max, equal to M/I/v, from which it follows that I/v=M/L max.

The resistance of the rod thus depends on I/v, that is to say the modulus of resistance on flexion.

The resistance in the proximal cylindrical section will thus be proportional to the modulus of resistance on flexion: I/v=πd³/32=12.27 mm³

The resistance in the distal rectangular section will also be proportional to the modulus of resistance on flexion, i.e.:

in the sagittal plane I z/v=b h²/6 in the frontal plane I y/v=hb²/6

In view of the specifications set down, and on the basis of the observations made with regard to breaks in rods already implanted, it is possible to establish an order of priority in the design of the rods, taking into account their resistance and their rigidity.

1. High resistance of the rods, in the sagittal plane:

that is to say high modulus of resistance on flexion

Mf=I z/v=b h²/6

2. Low rigidity of the rods, in the sagittal plane:

that is to say relative flexibility of the rods in the flexion movements, that is to say low second moment of area I f=Jz=bh³/12

3. High resistance of the rods, in the frontal plane:

that is to say high modulus of resistance on flexion

Ms=I z/v=h b2/6

4. High rigidity of the rods, in the frontal plane:

that is to say high second moment of area

I s=I y=h b³/12

Thus, to have great rigidity in the frontal plane, a high ratio hb³ will be necessary.

To have a rigidity which decreases in the sagittal plane, from proximal to distal, it will be necessary to have a ratio bh³ decreasing from proximal to distal.

To have a high resistance in the two planes, it will be necessary to have high hb² and bh² ratios. Each solution will therefore only be a compromise.

By giving different values to Mf, If, Ms and Is, it is possible to determine the different values for h and b.

The material cannot in fact be changed for the time being; there will therefore still be a YOUNG modulus equal to 200,000 N/mm². It is therefore only by acting on the shape of the rod, and more particularly on the distal rectangular shape, that is to say by acting on the values of h and b, that it is possible to satisfy these four priorities, classed from 1 to 4, established on the basis of the specifications.

Calculation of b and h, giving priority to the rigidity:

$$I_f = \frac{bh^3}{12} \quad \Longleftrightarrow \quad \frac{I_f}{I_s} = \frac{h^2}{b^2}$$

$$I_s = \frac{hb^3}{12} \quad \Longleftrightarrow \quad \boxed{h = b\sqrt{\frac{I_f}{I_s}}}$$

$$I_f = \frac{bh^3}{12} \quad \Longleftrightarrow \quad \frac{I_f}{I_s^3} = \frac{bh^3}{12} \times \frac{(12)^3}{h^3 b^9}$$

$$I_s^3 = \frac{h^3 b^9}{(12)^3} \quad \Longleftrightarrow \quad \frac{I_f}{I_s^3} = \frac{144}{b^8}$$

$$\Longleftrightarrow \quad \boxed{b = \sqrt[8]{144 \times \frac{I_s^3}{I_f}}}$$

Calculation of b and h, giving priority to the resistance:

$$M_f = \frac{bh^2}{6}$$

$$\Longleftrightarrow \quad \frac{M_f}{M_S} = \frac{h}{b}$$

$$M_S = \frac{hb^2}{6}$$

$$\boxed{h = b\frac{M_f}{M_S}}$$

$$M_f = \frac{bh^2}{6}$$

$$\Longleftrightarrow \quad \frac{M_f}{M_S^2} = \frac{bh^2}{6} \times \frac{36}{h^2 b^4}$$

$$M_S^2 = \frac{h^2 b^4}{36}$$

$$\Longleftrightarrow \quad \frac{M_f}{M_S} = \frac{6}{b^3}$$

$$\Longleftrightarrow \quad \boxed{b = \sqrt[3]{6 \times \frac{M_S^2}{M_f}}}$$

From the tests which have been carried out, it has been found that the number of breaks in rods according to the invention is considerably less compared to the number of breaks occurring with the rods of the prior art.

The surgical method for positioning this instrumentation is as follows:

Restoration of good lumbar lordosis and good dorsal kyphosis. The lumbar lordosis must be secured by arthrodesis in order to have a result which is stable over time, and a uniform development of the superjacent thoracic spine. The deformations in the frontal plane are, by contrast, minimal at the age when the operation is performed;

no dorsal arthrodesis, on the one hand, so as to diminish the consequences on vitality and prevent inhibition of growth, and, on the other hand, the equipment must be sufficiently flexible in the anteroposterior plane in order to permit balancing of the trunk.

By way of non-limiting example, it is difficult for the diameter of the cylindrical part to exceed 5.3 mm, since an increase in this diameter would make it necessary to replace the pedicular screws. In the case of children a limitation is imposed by the size of the pedicles on the one hand, and by the space taken up by the screw heads on the other hand.

Furthermore, the studies carried out have shown that the rigidity of the assembly is more important in the frontal plane than in the sagittal plane. It is the passage from a cylindrical section to a rectangular section, decreasing in the transition zone 8, and subsidiarily an increase in the number of DTT (Transverse Traction Device) which allows this advantage to be won.

It should be recalled that the rod proposed by the invention is adapted for surgery at an early stage. It is therefore necessary to operate on pliant and reducible scoliosis. It is in fact difficult for the rods of rectangular cross-section to be curved in the frontal plane and they could not be placed on spines affected by stiff and irreducible scoliosis. The concept of the rectangular cross-section of the dorsal part 7 of the rod 5 is thus inseparable from that of early surgery, that is to say, as has already been indicated, in children of approximately 11 to 13 years of age.

It is also advantageous for the hurled zone 9 to be interrupted a little before the start of the transition zone 8 so as not to accumulate the changes in shape at the same site and, in so doing, create a cause for decrease in the fatigue strength.

The invention is not limited to the embodiment described and can comprise various alternatives within the scope of the claims which follow.

We claim:

1. A vertebral instrumentation rod (5) having a first end and a second end and a solid cross-section from said first end to said second end for the fixation of an unstable spine, comprising:

a first elongated rod portion (6) defining a longitudinal axis (Ox), a sagittal plane (Ox, Oy) and a front plane (OX, Oz) perpendicular to the sagittal plane, both planes passing through said longitudinal axis, said first rod portion having a first length (L1) along said longitudinal axis and a substantially uniform first solid cross-section along said first length configured such that said first rod portion is substantially equally rigid in both the sagittal plane and the frontal plane; and a second elongated rod portion (7) integral with said first rod portion said second rod portion having a second length (L2) extending along said longitudinal axis and a second solid cross-section along said second length configured such that said second rod portion has a substantially different rigidity between the frontal plane and the sagittal plane.

2. The vertebral instrumentation rod of claim 1, wherein said second cross section is configured such that said second rod portion is substantially more rigid in said sagittal plane than in said frontal plane, whereby said second rod portion has a greater resistance to flexion in said frontal plane than in said sagittal plane.

3. The vertebral instrumentation rod of claim 1, wherein said second length is longer than said first length.

4. The vertebral instrumentation rod of claim 3, wherein said first length is sized to span the length of the lumbar vertebrae and said second length is sized to span along a substantial portion of the length of the dorsal vertebrae.

5. The vertebral instrumentation rod of claim 1, further comprising an elongated transition zone (8) integral with and between said first and second rod portions, said transition zone having a cross-section that varies along its length so that its second moment of area is substantially constant along its length.

6. The vertebral instrumentation rod of claim 1, wherein:

said first cross-section is circular; and said second cross-section is rectangular.

7. The vertebral instrumentation rod of claim 6 wherein said rectangular second cross-section has a height (h) in the frontal plane and a width (b) in the sagittal plane, said width being greater than said height.

8. The vertebral instrumentation rod of claim 6, wherein:

said circular first cross-section has a diameter;

said height of said second cross-section is less than said diameter; and said width of said second cross-section is greater than said diameter.

9. The vertebral instrumentation rod of claim 6, further comprising an elongated transition zone (8) integral with and between said first and second rod portions, said transition zone having a third cross-section that varies along its length and configured so that its second moment of area is substantially constant along its length.

10. The vertebral instrumentation rod of claim 9, wherein said third cross-section of said transition zone is circular at a first end connected to said first rod portion and is rectangular at a second end connected to said second rod portion, said third cross-section having a height in the frontal plane and a width in the sagittal plane, said height and width varying along the length of said transition zone between said circular first end and said rectangular second end.

11. The vertebral instrumentation rod of claim 10, wherein said height of said transition zone decreases from said first end to said second end.

12. The vertebral instrumentation rod of claim 11, wherein said width of said transition zone increases from said first end to said second end.

13. The vertebral instrumentation rod of claim 10, wherein said width of said transition zone increases from said first end to said second end.

14. The vertebral instrumentation rod of claim 1, wherein said second cross-section of said second rod portion varies along said second length from a first end integral with said first rod portion to a distal free second end.

15. The vertebral instrumentation rod of claim 14, wherein said second cross-section of said second rod portion is rectangular having a height (h) in the frontal plane and a width (b) in the sagittal plane, said height decreasing from said first end to said second end of said second rod portion.

16. The vertebral instrumentation rod of claim 15, wherein said width of said second cross-section increases from said first end of said second rod portion along a portion of said second length, and said width then decreasing along a remaining portion of said second length to said second end of said second rod portion.

17. The vertebral instrumentation rod of claim 14, wherein said second cross-section of said second rod portion is rectangular having a height (h) in the frontal plane and a width (b) in the sagittal plane, said width increasing from said first end of said second rod portion along a portion of said second length, and said width then decreasing along a remaining portion of said second length to said second end of said second rod portion.

18. The vertebral instrumentation rod of claim 1, wherein said first rod portion includes a toughened surface (9) along a portion of said first length.

19. Instrumentation for the fixation of the spine, comprising:

a vertebral rod (5); and a plurality of bone engaging fasteners (3,4) for coupling said vertebral rod to the spine, wherein said vertebral rod includes a first elongated rod portion (6) defining a longitudinal axis (Ox), a sagittal plane (Ox, Oy) and a frontal plane (Ox, Oz) perpendicular to the sagittal plane, both planes passing through said longitudinal axis, said first rod portion having a first length (L1) along said longitudinal axis and a substantially uniform first solid cross-section along said first length configured such that said first rod portion is substantially equally rigid in both the sagittal plane and the frontal plane; and a second elongated rod portion (7) integral with said first rod portion said second rod portion having a second length (L2) extending along said longitudinal axis sized to support a number of said fasteners and a second solid cross-section along said second length configured such that said second rod portion has a substantially different rigidity between the frontal plane and the sagittal plane.

20. The instrumentation of claim 19, wherein said second cross section is configured such that said second rod portion is substantially more rigid in said sagittal plane than in said frontal plane, whereby said second rod portion has a greater resistance to flexion in said frontal plane than in said sagittal plane.

21. The instrumentation of claim 19, wherein said vertebral rod further includes an elongated transition zone (8) integral with and between said first and second rod portions, said transition zone having a third cross-section that varies along its length and configured so that its second moment of area is substantially constant along its length.

22. The vertebral instrumentation rod of claim 21, wherein said third cross-section of said transition zone is circular at a first end connected to said first rod portion and is rectangular at a second end connected to said second rod portion, said third cross-section having a height in the frontal plane and a width in the sagittal plane, said height and width varying along the length of said transition zone between said circular first end and said rectangular second end.

23. The vertebral instrumentation rod of claim 22, wherein said height of said transition zone decreases from said first end to said second end, and said width of said transition zone increases from said first end to said second end.

24. The vertebral instrumentation rod of claim 19, wherein said second length is longer than said first length, and said first length is sized to span the length of the lumbar vertebrae and said second length is sized to span along a substantial portion of the length of the dorsal vertebrae.

25. The vertebral instrumentation rod of claim 19 wherein:

said first cross-section is circular; and said second cross-section is rectangular.

26. The vertebral instrumentation rod of claim 25 wherein said rectangular second cross-section has a height (h) in the frontal plane and a width (13) in the sagittal plane, said width being greater than said height.

27. The vertebral instrumentation rod of claim 25, wherein:

said circular first cross-section has a diameter;

said height of said second cross-section is less than said diameter; and said width of said second cross-section is greater than said diameter.

28. The vertebral instrumentation rod of claim 19, wherein said second cross-section of said second rod portion varies along said second length from a first end integral with said first rod portion to a distal free second end, and said second cross-section of said second rod portion is rectangular having a height (h) in the frontal plane and a width (b) in the sagittal plane, said height decreasing from said first end to said second end of said second rod portion.

29. The vertebral instrumentation rod of claim 19, wherein said first rod portion includes a roughened surface (9) along a portion of said first length.

* * * * *